(12) United States Patent
Mass et al.

(10) Patent No.: US 7,613,521 B2
(45) Date of Patent: Nov. 3, 2009

(54) TELEMETRY FOR A BATTERY OPERATED DEVICE

(75) Inventors: William Robert Mass, Maple Grove, MN (US); Jay William Axelrod, Minneapolis, MN (US); Jason Allen Malone, Lino Lakes, MN (US); Richard Earl Stein, Edina, MN (US); Robert Joseph Gaskill, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 180 days.

(21) Appl. No.: 10/758,832

(22) Filed: Jan. 16, 2004

(65) Prior Publication Data

US 2005/0159105 A1 Jul. 21, 2005

(51) Int. Cl.
*A61N 1/00* (2006.01)
(52) U.S. Cl. ........................................ 607/60
(58) Field of Classification Search .................. 607/60, 607/61, 30, 137; 320/103; 323/347
See application file for complete search history.

(56) References Cited

U.S. PATENT DOCUMENTS

| | | | | |
|---|---|---|---|---|
| 4,323,074 A | * | 4/1982 | Nelms | .......................... 607/30 |
| 5,122,729 A | * | 6/1992 | Itoga et al. | ................... 323/347 |
| 5,279,292 A | * | 1/1994 | Baumann et al. | ............. 607/137 |
| 5,769,877 A | * | 6/1998 | Barreras, Sr. | ................. 607/61 |
| 5,807,397 A | * | 9/1998 | Barreras | ....................... 607/61 |
| 6,552,511 B1 | * | 4/2003 | Fayram | ....................... 320/103 |
| D490,525 S | | 5/2004 | Stein et al. | |
| 6,993,393 B2 | * | 1/2006 | Von Arx et al. | ................ 607/60 |
| 2003/0135246 A1 | | 7/2003 | Mass et al. | |
| 2004/0230246 A1 | | 11/2004 | Stein et al. | |
| 2004/0230247 A1 | | 11/2004 | Stein et al. | |
| 2005/0131479 A1 | | 6/2005 | Axelrod et al. | |
| 2005/0159105 A1 | | 7/2005 | Mass et al. | |

* cited by examiner

*Primary Examiner*—George Manuel
(74) *Attorney, Agent, or Firm*—Schwegman, Lundberg & Woessner, P.A.

(57) ABSTRACT

The present invention relates to a wireless handheld device that is configured to communicate with an implanted device using inductive telemetry. The handheld device is preferably battery operated and includes a battery powered controller and a battery powered inductive coil. The inductive coil is configured to communicate with an inductive coil of the implanted device using inductive telemetry. The handheld device may include one battery voltage source that powers both the controller and the inductive coil, or multiple battery voltage sources to power the controller and inductive coil separately. In a single battery voltage source embodiment, the voltage may be amplified or reduced to meet the power needs of the controller and inductive coil. In a multiple battery voltage source embodiment, the voltage sources may be combined to increase the power output requirements of the inductive coil.

21 Claims, 3 Drawing Sheets

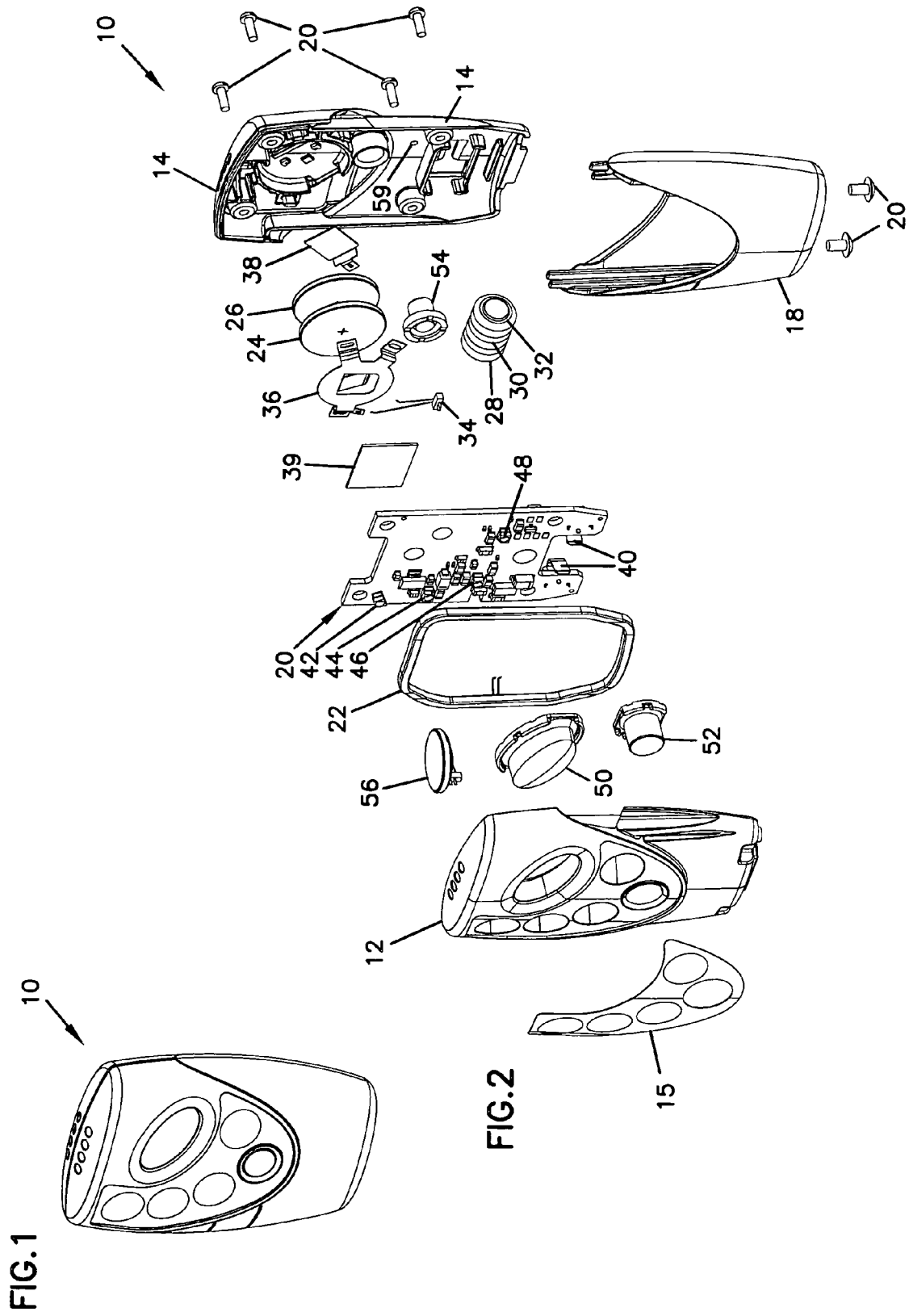

TELEMETRY FOR A BATTERY OPERATED DEVICE

BACKGROUND OF THE INVENTION

1. Field of the Invention

The invention generally relates to communication devices, and more specifically relates to wireless handheld devices that communicate using inductive telemetry.

2. Related Art

Implantable medical devices are becoming increasingly versatile and able to perform many different physiological sensing functions that enable a clinician to quickly and accurately assess patient health. Traditionally, an accurate assessment of patient health required the clinician to synthesize often divergent or seemingly unrelated indications of patient health. For example, a diagnosis of congestive heart failure might include not only an assessment and evaluation of cardiac function data, but also an evaluation of other physiological factors like patient fatigue or respiration data.

Typically, a clinician will assess patient health by inquiring how the patient feels or asking about the patient's activities and then make an indirect assessment based on the patient's response and the clinician's observation of the patient's appearance. However, these measures are very subjective and are limited to the time of the patient/clinician interaction and the quality of patient recall or willingness to divulge information. These factors affect the quality of the assessment.

Modern implantable medical devices offer objective data to help the clinician assess patient health. Modern medical devices can sense and analyze physiological factors with improved accuracy and report that sensed and analyzed information to the clinician or the patient. The data or information that a medical device reports in the form of a sensed physiological parameter can be characterized as either derived or non-derived data. Non-derived data can be understood as raw biometric information sensed by the medical device that has not been clinically analyzed to any meaningful degree. For example, non-derived biometric information may comprise the quantified measurement of a patient's heart rate or blood pressure. In contrast, derived data is biometric information that has been analyzed and perhaps assigned some qualitative value. For example, as a medical device senses a patient's cardiac cycle and clinically analyzes that information, the medical device may report that an arrhythmia has occurred as the result of sensing and analyzing a cardiac rhythm outside expected parameters. Other derived sensors may include the cumulative calories burned by daily activity, a weight loss monitor, a participation in activities monitor, a depression monitor, or determining the onset of cancer, all of which may be ascertained by sensing physiological data and analyzing that data by using clinically derived algorithms or other analytical methods.

Some implanted medical devices may be part of an advanced Patient Management System that includes various physiological sensors and other features to sense and report patient data. Such a system may be adapted to analyze the sensed data in a manner that yields an accurate assessment or prediction of patient health or relative well-being. In this way, the system can be configured to report not only a relative state of patient health, but also alert the clinician to patient health degradation before the onset of an acute episode.

Accurate and reliable reporting and collection of the most relevant data produced by the above-mentioned medical devices and systems has proven to be difficult and cumbersome in many instances. One drawback of many implanted medical devices is their finite memory available for storage of collected data. Some devices include a rolling memory that stores a limited amount of data, which, if not downloaded from the device in a predetermined time period, is dropped from the memory as it is replaced with newer, incoming data.

Typically, a doctor or clinician must perform data retrieval from a medical device or system during a formal visit and evaluation of the patient. Because of the infrequency of these types of patient visits, much of the data collected by the medical device or system is lost before being retrieved and analyzed by the doctor. Of particular concern is the loss of data related to an important physiological event such as heart failure, asthma attacks, etc., whether or not the occurrence of these events are known to the patient.

A data retrieval mechanism that effectively captures relevant physiological data from an implanted medical device or system would be an important advance in the art.

SUMMARY OF THE INVENTION

One aspect of the invention relates to a wireless handheld device that is configured to communicate with an implanted device using inductive telemetry. The handheld device includes a battery powered controller and a battery powered inductive coil that is controlled by the controller. The inductive coil is configured to communicate with an inductive coil of the implanted device using inductive telemetry. The handheld device may include one battery voltage source that powers both the controller and the inductive coil, or may include multiple battery voltage sources that power the controller and inductive coil separately. In a single battery voltage source embodiment, the voltage provided by the battery voltage source may be amplified or reduced to meet the power needs of the controller and inductive coil. In a multiple battery voltage source embodiment, the voltage sources may be combined to meet the power output requirements of the inductive coil.

BRIEF DESCRIPTION OF THE DRAWINGS

FIG. 1 is a perspective view of one embodiment of a personal handheld data retrieval device that incorporates principles of the present invention.

FIG. 2 is an exploded perspective view of the device shown in FIG. 1.

DETAILED DESCRIPTION OF THE PREFERRED EMBODIMENT

Figure 3:
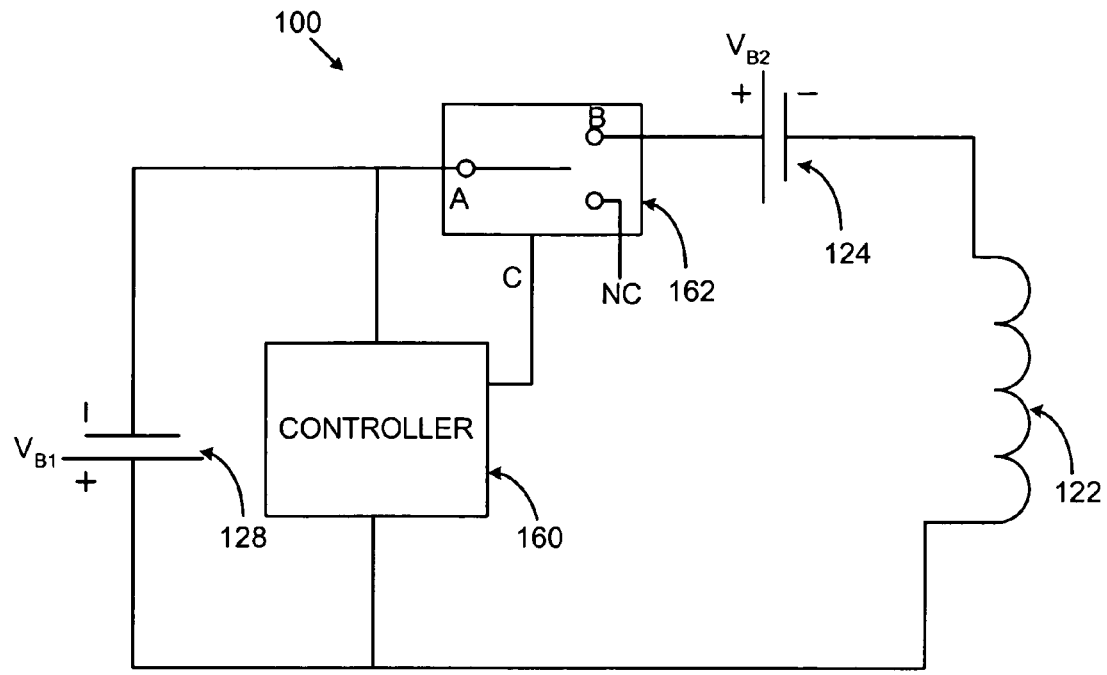
FIG. 3 is a schematic circuit diagram representing features of one embodiment of the present invention with multiple battery voltage sources.

The present invention relates to a wireless handheld device that is configured to communicate with an implanted device using inductive telemetry. The handheld device is preferably battery operated and includes a battery powered controller and a battery powered inductive coil. The inductive coil is configured to communicate with an inductive coil of the implanted device using inductive telemetry. The handheld device may include one battery voltage source that powers both the controller and the inductive coil, or multiple battery voltage sources to power the controller and inductive coil separately. In a single battery voltage source embodiment, the voltage may be amplified or reduced to meet the power needs of the controller and inductive coil. In a multiple battery voltage source embodiment, the voltage sources may be combined to meet the power output requirements of the inductive coil.

A personal handheld device that uses inductive telemetry may be advantageous for several reasons. Many known implantable medical devices use inductive telemetry as a communication medium. Inductive telemetry is a safe, simple and effective medium for communication between devices, whether the devices are implanted or not. Typically, an implanted device with inductive telemetry capabilities communicates with a programmer via some sort of "wand" or other mobile device that is hard wired to the programmer for purposes of powering the wand and communication of information back and forth between the controller and the implanted device. Because of the cost and immobility of the controller, a patient with an implanted device typically has to visit a doctor or be visited by a clinician of some type in order for the inductive telemetry communication to take place. Furthermore, known "wands" or the like inductive telemetry devices for communicating with the implanted device have high power requirements and are not well suited for mobile use by a patient.

The present invention addresses these and other disadvantages of known devices and systems for retrieving data from an implanted device, some of which are described in the above background section. The present invention is configured for use by a patient and is capable of operation using battery power. The present invention is compact, mobile, relatively easy to use, and includes circuitry and control electronics that are simple and compatible with many known controllers and implantable devices.

On example of a handheld device of the present invention is device 10 shown in FIGS. 1 and 2. Device 10 includes a front cover 12 with an overlay 15, rear cover 14, first fasteners 16 that secure the front and rear covers 12, 14 together, a bottom cover 18, and second fasteners 20 that secure bottom cover 18 to the combined front and rear covers 12, 14. Device 10 also includes an inductive coil 22, telemetry batteries 24, 26, and system batteries 28, 30, 32. A plug harness 34, a battery clip 36, and a bottom contact 38 are associated with telemetry batteries 24, 26.

Device 10 may also include a printed circuit board (PCB) assembly 20 to which many of the electronic components of device 10 are mounted. PCB 20 may include system battery leads 40 for the system batteries 28, 30, 32, and LEDs 42, 44, 46, 48 that show through front cover 12 when illuminated. PCB 20 may also include a controller, an amplifier, a reducer, and one or more switches, all of which are not clearly identified in FIG. 2, but may be included on either a front or rear primary surface of PCB 20. The purpose of a controller, amplifier, reducer, and switch are described with reference to the example circuits shown in FIGS. 3-5.

Activating buttons of device 10 may be used to control various functions of the device. Device 10 may include an inquiry button 50, a therapy button 52, and a volume button 54. Device 10 preferably also includes some type of reset button (not shown) that is positioned within device 10 at a location so as not to be inadvertently activated. The reset button may be mounted to PCB 20 and accessible through, for example, a small aperture 59 in rear cover 14 (see FIG. 2). When engaged, the reset button typically activates a boot load or similar reset mode of device 10.

Device 10 may also include a speaker that provides audible messages from the device, and an insulator 58 positioned between telemetry batteries 24, 26 and components mounted to PCB 20. Device 10 may also be configured to be compatible with alternative features and structure that are not shown in FIGS. 1 and 2, but that may be advantageous for purposes related to inductive telemetry.

Device 10 is preferably a compact, light-weight and relatively easy to use device. With those characteristics in mind, various features of device 10 have a relatively compact, light-weight and easy-to-use configuration. For example, telemetry batteries 24, 26 are preferably relatively high voltage (greater than 2 volts per battery), low-profile batteries that have a relatively long life as compared to other types of batteries, such as silver oxide batteries. An example of such a battery is a low-profile 3-volt lithium battery. In some configurations, telemetry batteries 24, 26 may be reduced to a single battery having a voltage of about 2 to 12 volts, and preferably about 6 volts. Telemetry batteries 24, 26 are shown in FIG. 2 as being positioned between front and rear covers 12, 14 such that device 10 must be disassembled completely in order to replace the telemetry batteries. In other embodiments, telemetry batteries 24, 26 may be positioned within device 10 in such a way as to be more easily accessible and replaceable, such as by the removal of a battery cover that provides access to batteries 24, 26.

System batteries 28, 30, 32 may also be low-voltage, low-profile batteries. Preferably, each of system batteries 28, 30, 32 provide a voltage of 1 to 3 volts and preferably about 1.5 volts so that the net voltage from the system batteries is about 3 to 6 volts. The system batteries may be relatively inexpensive silver-oxide batteries, more expensive, longer-life batteries such as lithium batteries, or may be any suitable type of rechargeable batteries. Rear cover 14 may include a battery opening with an individual cover for relatively quick and easy replacement of system batteries 28, 30, 32 within device 10 without having to disassemble device 10. In other embodiments, the system batteries may be replaced with 1, 2, 4 or more batteries, and may be mounted in the hand-held device in a less accessible position that requires disassembly of the device.

Telemetry batteries 24, 26 are intended primarily to power inductive coil 22 for the purpose of inductive telemetry communication between device 10 and another device, such as an implanted device or a programmer. System batteries 28, 30, 32 are preferably intended to powering electronic components, such as those mounted to PCB 20, and may, in some configurations, be combined in series with telemetry batteries 24, 26 to provide greater power to inductive coil 22. Alternative embodiments with various combinations of batteries and other electronic features are described below with reference to the schematic circuit diagrams of FIGS. 3-5.

Device 100 illustrated in the circuit diagram of FIG. 3 includes an inductive coil 122, a first battery voltage source 128, a second battery voltage source 124, a controller 160, and a switch 162. Circuit 100 essentially represents the basic electronic features of device 10. First battery voltage source 128 provides a voltage ($V_{B1}$) for powering controller 160, and second battery voltage source 124 provides a voltage ($V_{B2}$) that meets the power requirements of inductive coil 122. The switch 162 includes an input line A from the first voltage source 128, an input line B from the second voltage source 124, and a non-connect line (NC). The switch 162 is controlled by controller 160 via a control line C to facilitate the combination of voltages from first and second battery voltage sources 128, 124 to generate a greater effective voltage output ($V_{B1}+V_{B2}$) for powering inductive coil 122. Typically, it is preferred to have the greatest voltage possible for powering inductive coil 122 to improve telemetry communication between device 100 and another device such as, for example, a separate controller or an implanted device.

Figure 4:
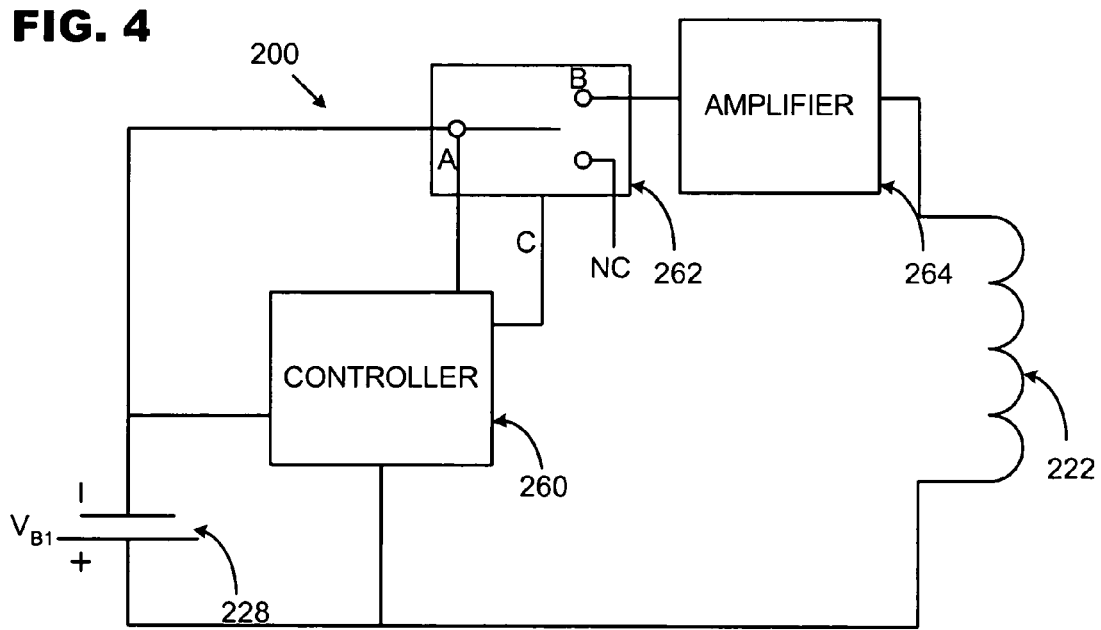
FIG. 4 is a schematic circuit diagram representing features of another embodiment of the present invention having a single battery voltage source.

Another circuit 200 representing an alternative configuration of the present invention is shown in FIG. 4. Circuit 200 includes an inductive coil 222, a battery voltage source 228, a controller 260, a switch 262, and an amplifier 264. The switch 262 includes an input line A from the battery voltage source 128, an input line B from the amplifier 264, and a non-connect line (NC). The voltage ($V_{B1}$) provided by battery voltage source 228 is preferably sufficient to operate the controller 260. Because the voltage required to power controller 260 is often less than the required voltage to power inductive coil 222, the amplifier 264 may be used to amplify the voltage of battery voltage source 228 when inductive coil 222 is in use. In operation, controller 260 may activate switch 262 via control line C to connect battery voltage source 228 to amplifier 264 to increase (power up) the effective voltage provided to inductive coil 222.

Figure 5:
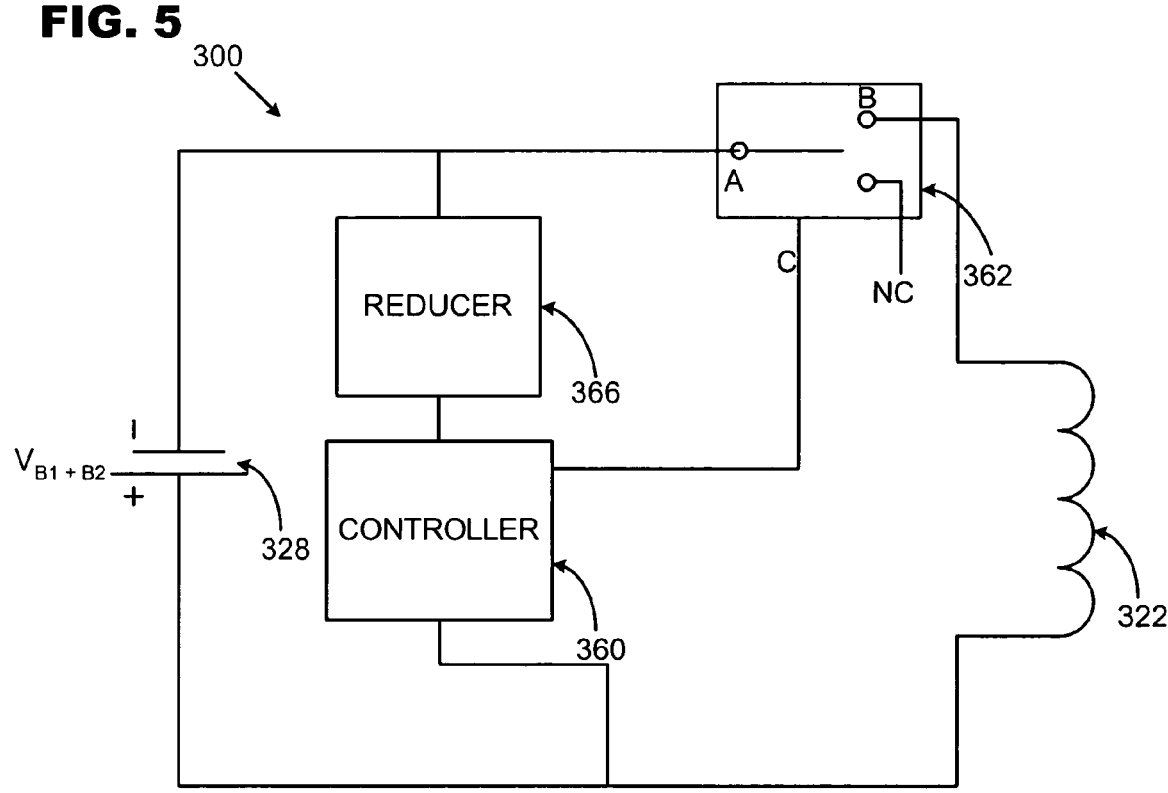
FIG. 5 is a schematic circuit diagram representing features of yet another embodiment of the present invention having a single battery voltage source.

A further embodiment of the present invention is represented by circuit 300 illustrated in FIG. 5. Circuit 300 includes an inductive coil 322, a battery voltage source 328, a controller 360, a switch 362, and a reducer 366. The switch 362 includes an input line A from the battery voltage source 328, an input line B from the inductive coil 322, and a non-connect line (NC). In this embodiment, battery voltage source 328 preferably provides a voltage ($V_{B1}+V_{B2}$) sufficient to power inductive coil 322. Because the voltage required to power inductive coil 322 is typically greater than the voltage required to power controller 360, reducer 366 may be used to decrease (power down) the voltage provided to controller 360. In operation, controller 360 may control switch 362 via a control line C so that inductive coil 322 is provided with voltage from battery voltage source 328 only when inductive coil 322 is in use.

Although there may be some advantages to providing a single, high-voltage battery source 328 for circuit 300, at least one disadvantage of such a configuration is that a large amount of power may be wasted by having to reduce the voltage provided to controller 360. Since controller 360 is typically in almost continuous use, or at least more consistently using voltage than inductive coil 322, it may be less advantageous in some respects to use the configuration of circuit 300 than the configuration of circuit 200 that also uses a single battery voltage source 228.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A handheld device configured to communicate data with an implanted device using inductive telemetry, comprising:
    a first battery voltage source;
    a second battery voltage source;
    a battery powered telemetry coil electrically connected in series with the second battery voltage source;
    a battery powered controller electrically connected to the first battery voltage source to be powered by the first battery voltage source;
    a switch configured to, in response to a control signal, selectively connect the first battery voltage source in series with the second battery voltage source to power the battery powered telemetry coil;
    wherein the controller is configured to provide the control signal to drive the telemetry coil for telemetry communication, and wherein the controller is configured to transmit and receive data to and from a telemetry coil of the implanted device using inductive telemetry.

2. The handheld device of claim 1, wherein the first battery voltage source powers the controller and drives the telemetry coil.

3. The handheld device of claim 2, further comprising a voltage amplifying device that amplifies a voltage from the first battery voltage source that is provided to the telemetry coil.

4. The handheld device of claim 2, further comprising a voltage reducing device that reduces a voltage from the first battery voltage source that is provided to the controller.

5. The handheld device of claim 1, wherein the first battery voltage source provides a voltage of about 2 to 6 V and the second battery voltage source provides a voltage of about 2 to 12 V.

6. The handheld device of claim 1, wherein the first battery voltage source includes at least one silver oxide battery.

7. The handheld device of claim 1, wherein the second battery voltage source includes at least one low profile lithium battery.

8. A circuit for a wireless handheld device configured for communicating data with inductive telemetry, comprising:
    a first battery voltage source;
    a controller in parallel with the first battery voltage source;
    a telemetry coil driven by the first battery voltage source and controllable by the controller to transmit and receive data to and from a second device using inductive telemetry; and
    a second battery voltage source connected in series with the first voltage source, wherein the first battery voltage source powers the controller and the second voltage battery source drives the telemetry coil.

9. The circuit of claim 8, further comprising a switch connected between the first and second voltage battery sources, wherein the controller controls the switch between an open position and a closed position, and when the switch is in the closed position the effective voltage provided to drive the telemetry coil is equal to the voltage of the first battery voltage source plus the voltage of the second battery voltage source.

10. The circuit of claim 8, wherein the wireless handheld device is adapted to receive sensed physiological parameters from the second device.

11. The circuit of claim 8, wherein the first battery voltage source, the controller, the telemetry coil, and a switch are mounted on a printed circuit board.

12. A method of powering a handheld device configured for communicating data with a second device using inductive telemetry, the handheld device including a controller, a telemetry coil, and a first battery voltage source, the method comprising:
    connecting the controller in parallel with the first battery voltage source;
    connecting the telemetry coil to the controller and driven by the first battery voltage source; and
    activating the telemetry coil in the handheld device to facilitate inductive telemetry for transmitting and receiving data to and from the second device,
    wherein the handheld device further includes a second battery voltage source connected in series with the first battery voltage source, wherein the telemetry coil is activated using increased voltage provided by the first and second battery voltage sources in series.

13. The method of claim 12, wherein the handheld device further comprises a switch connected between the battery voltage source and the telemetry coil, the method further comprising the step of opening and closing the switch to control operation of the telemetry coil.

14. The method of claim 13, further comprising:
receiving sensed physiological parameters from the second device.

15. The method of claim 14, wherein the sensed parameters includes derived data.

16. The method of claim 14, wherein the sensed parameters includes non-derived data.

17. A method of powering a handheld device having a controller, a telemetry coil, and at least one battery providing a battery voltage, the method comprising the steps of:
powering the controller and the telemetry coil with the battery voltage; and
transmitting and receiving data to and from an implanted device using inductive telemetry,
wherein the handheld device includes a first battery providing a first battery voltage, and a second battery providing a second battery voltage, the controller being powered by the first battery voltage and the telemetry coil being driven by the second battery voltage and wherein the telemetry coil is driven by a series combination of the first and second battery voltages.

18. The method of claim 17, wherein the handheld device further comprises a switch connected between the first and second batteries, and the controller controls opening and closing of the switch to determine a battery voltage provided to the telemetry coil.

19. The method of claim 17, further comprising:
receiving sensed physiological parameters from the implanted device.

20. A handheld device configured to communicate data with an implanted device using inductive telemetry, comprising:
a battery powered controller;
a battery powered telemetry coil controlled by the controller and configured to transmit and receive data to and from a telemetry coil of the implanted device using inductive telemetry;
a battery voltage source that powers the controller and the telemetry coil, the battery voltage source adapted to provide a first potential; and
means for adapting the first potential to provide a second potential for use in powering the controller or the telemetry coil,
wherein the means for adapting the first potential includes a voltage amplifying device adapted to amplify the first potential to provide the second potential to power the telemetry coil.

21. The handheld device of claim 20, wherein the means for adapting the first potential includes a voltage reducing device adapted to reduce the first potential to provide the second potential to power the controller.

* * * * *

UNITED STATES PATENT AND TRADEMARK OFFICE
CERTIFICATE OF CORRECTION

PATENT NO. : 7,613,521 B2 Page 1 of 1
APPLICATION NO. : 10/758832
DATED : November 3, 2009
INVENTOR(S) : William R. Mass et al.

It is certified that error appears in the above-identified patent and that said Letters Patent is hereby corrected as shown below:

In column 4, line 62, delete "160 via a control" and insert -- 160 via control --, therefor.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,613,521 B2                              Page 1 of 1
APPLICATION NO. : 10/758832
DATED            : November 3, 2009
INVENTOR(S)      : Mass et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this

Nineteenth Day of October, 2010

David J. Kappos
*Director of the United States Patent and Trademark Office*